US012582307B2

(12) United States Patent
Yasumi et al.

(10) Patent No.: US 12,582,307 B2
(45) Date of Patent: Mar. 24, 2026

(54) IMAGE CAPTURING DEVICE AND IMAGE CAPTURING SYSTEM

(71) Applicant: AILLIS INC., Tokyo (JP)

(72) Inventors: Takashi Yasumi, Tokyo (JP); Takashi Kinouchi, Tokyo (JP); Akiho Sakuma, Tokyo (JP); Fuminari Hasegawa, Kobe (JP)

(73) Assignee: AILLIS INC. (JP)

( * ) Notice: Subject to any disclaimer, the term of this patent is extended or adjusted under 35 U.S.C. 154(b) by 219 days.

(21) Appl. No.: 18/491,991

(22) Filed: Oct. 23, 2023

(65) Prior Publication Data

US 2024/0041311 A1    Feb. 8, 2024

Related U.S. Application Data

(63) Continuation of application No. PCT/JP2021/016891, filed on Apr. 28, 2021.

(51) Int. Cl.
| | |
|---|---|
| *A61B 1/04* | (2006.01) |
| *A61B 1/06* | (2006.01) |
| *A61B 1/24* | (2006.01) |

(52) U.S. Cl.
CPC .............. *A61B 1/24* (2013.01); *A61B 1/042* (2013.01); *A61B 1/0655* (2022.02)

(58) Field of Classification Search
CPC ......... A61B 1/24; A61B 1/042; A61B 1/0655; A61B 1/07; A61B 1/00034;
(Continued)

(56) References Cited

U.S. PATENT DOCUMENTS

2002/0077528 A1*  6/2002  Landgraf ................. A61B 1/24
600/131
2002/0097323 A1    7/2002  Ito
(Continued)

FOREIGN PATENT DOCUMENTS

| EP | 2074951 A2 | 7/2009 |
|---|---|---|
| JP | 2002-218286 A | 8/2002 |

(Continued)

OTHER PUBLICATIONS

European Search Report issued in the corresponding European Patent Application No. 21939245.3; dated Jan. 31, 2025 (total 15 pages).

*Primary Examiner* — Howard D Brown, Jr.
(74) *Attorney, Agent, or Firm* — Harness, Dickey & Pierce, P.L.C.

(57) ABSTRACT

An image capturing device and an image capturing system are provided for capturing images in the oral cavity. The image capturing device includes: a columnar main body having a prescribed length between the base and leading ends, the longitudinal direction of the main body follows the direction in which the main body is inserted into the oral cavity; a grip disposed on the same line as the main body on the base end side; a camera for capturing a subject image based on reflected light radiated from a light source and reflected by the oral cavity, the camera being disposed on the same line as the main body either inside the main body or closer to the base end than the main body; and a display for displaying the subject image captured by the camera, the display being disposed on the same line as the main body.

17 Claims, 14 Drawing Sheets

(58) Field of Classification Search
CPC ............ A61B 1/00052; A61B 1/00108; A61B
1/00135; A61B 5/0088; A61C 19/04;
A61C 9/0046; A61C 9/0053; G06F 3/14;
G06F 17/00; G06T 1/0007
See application file for complete search history.

(56) References Cited

U.S. PATENT DOCUMENTS

| | | | |
|---|---|---|---|
| 2005/0003323 A1 | 1/2005 | Katsuda et al. | |
| 2005/0019722 A1* | 1/2005 | Schmid ................... | A61B 1/24 |
| | | | 433/29 |
| 2009/0076321 A1* | 3/2009 | Suyama ............. | A61B 1/00052 |
| | | | 348/E5.025 |
| 2012/0281135 A1 | 11/2012 | Gebhardt | |
| 2014/0272764 A1* | 9/2014 | Miller ................... | A61B 1/051 |
| | | | 433/29 |
| 2019/0011996 A1* | 1/2019 | Sabina ................ | G06F 3/04883 |
| 2019/0029522 A1* | 1/2019 | Sato .......................... | G06T 7/75 |
| 2021/0196152 A1* | 7/2021 | Saphier ............. | A61B 1/00006 |
| 2022/0233284 A1* | 7/2022 | Fridman ................ | G16H 50/50 |
| 2023/0263397 A1* | 8/2023 | Van Der Poel ...... | A61B 5/0077 |
| | | | 433/29 |
| 2024/0023800 A1* | 1/2024 | Fridman ............ | A61B 1/00052 |

FOREIGN PATENT DOCUMENTS

| | | |
|---|---|---|
| JP | 2002-238849 A | 8/2002 |
| JP | 2004-081845 A | 3/2004 |
| JP | 2007-316528 A | 12/2007 |
| JP | 2010-197510 A | 9/2010 |
| JP | 2018-175722 A | 11/2018 |
| WO | 2019-131327 A1 | 7/2019 |

* cited by examiner

<u>1</u>

100

200

400

300

<u>400</u>

400

IMAGE CAPTURING DEVICE AND IMAGE CAPTURING SYSTEM

CROSS-REFERENCE TO RELATED APPLICATIONS

The present application is a continuation application of International Application No. PCT/JP2021/16891, filed on Apr. 28, 2021, which is expressly incorporated herein by reference in its entirety.

BACKGROUND

Technical Field

The present disclosure relates to an image capturing device and an image capturing system for capturing images of an inside of the oral cavity of a target person.

Related Art

Conventionally, it is known that physicians observe a change in a state of the oral cavity of a target person, and make diagnoses of, for example, viral cold. Japanese Patent Publication No. JP 2018-175722 A describes an intraoral image capturing system that is capable of capturing an image of an inside of the oral cavity. In such an intraoral image capturing system, a light camera subunit that includes a camera is moved to the front of the oral cavity by operating a handle that is disposed around the camera, and an image of a prescribed portion in the oral cavity is captured. Furthermore, the captured image is output on a monitor that is provided separately from the light camera subunit.

SUMMARY

In view of the technique described above, it is an object of the present disclosure to provide an image capturing device and an image capturing system better suited for capturing images in the oral cavity according to various embodiments.

In one aspect of the present disclosure, an "image capturing device including: a main body including a base end and a leading end, being formed in an approximately columnar shape having a prescribed length between the base end and the leading end, a longitudinal direction of the main body being located along a direction of insertion into an oral cavity to enable at least the leading end to be inserted into the oral cavity; one or more light sources configured to apply light having a prescribed frequency band toward the oral cavity, the one or more light sources being disposed closer to the base end than the main body or inside the main body to apply light having a prescribed frequency band toward the oral cavity; a grip configured to be grasped by a user, the grip being formed in an approximately columnar shape having a prescribed length along the longitudinal direction of the main body on a side of the base end of the main body, the grip and the main body being disposed on an identical straight line; a camera configured to capture a subject image on a basis of reflected light applied from the one or more light sources and reflected on the oral cavity, the camera being disposed closer to the base end than the main body or inside the main body, the camera and the main body being disposed on the identical straight line; and a display configured to display the subject image captured by the camera, the display being disposed on a side opposite to the oral cavity of the grip, the display and the main body being disposed on the identical straight line" is provided.

In one aspect of the present disclosure, an "image capturing system including: the image capturing device described above; and a processing device configured to process a subject image captured by the image capturing device, the processing device being communicably connected to the image capturing device in a wired or wireless manner" is provided.

According to various embodiments of the present disclosure, an image capturing device and an image capturing system better suited to capturing images in the oral cavity can be provided.

Note that the effects described above are illustrative for convenience of description, and are not restrictive. In addition to the effects described above or instead of the effects described above, any effects described in the present disclosure or effects that would be obvious to those skilled in the art can be exhibited.

DESCRIPTION OF EXEMPLARY EMBODIMENTS

Figure 1:
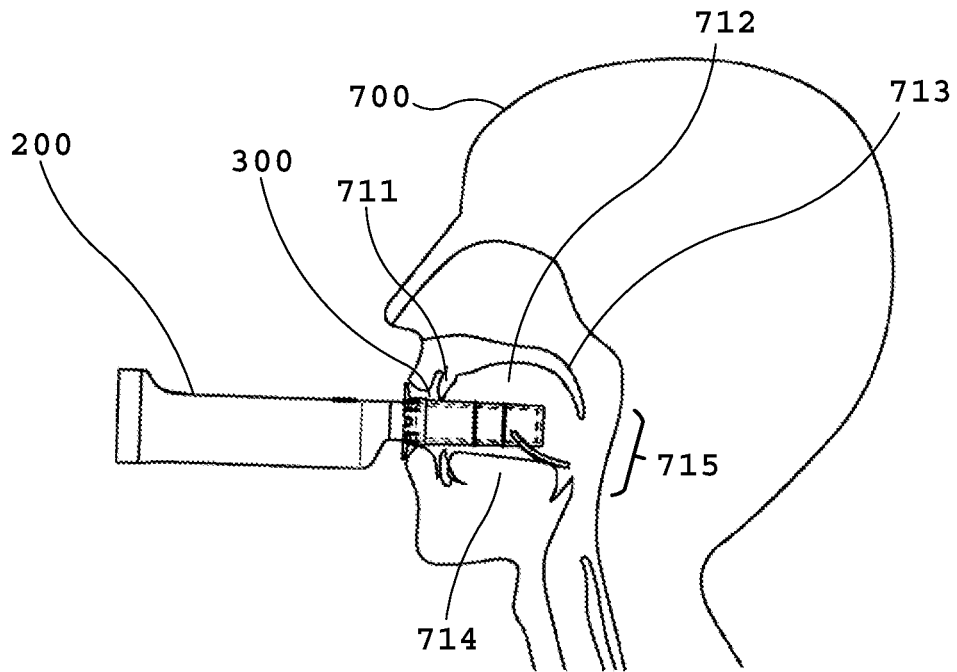
FIG. 1 is a diagram illustrating a use state of an image capturing system 1 according to an embodiment of the present disclosure.

Various embodiments of the present disclosure will be described with reference to the attached drawings. Note that components that are common in the drawings are denoted by the same reference sign.

First Embodiment

1. Outline of Image Capturing System 1

An image capturing system 1 according to the present disclosure is used to principally capture an image of an inside of the oral cavity of an examinee, and obtain a subject image. In particular, the image capturing system 1 is used to capture an image of the periphery of a deep side of a throat of the oral cavity and specifically, the pharynx. Accordingly, hereinafter, a case where the image capturing system 1 according to the present disclosure is used to capture an image of the pharynx will be principally described. However, the pharynx is an example of an imaged portion, and it is natural that the image capturing system 1 according to the present disclosure also be suitably used for another portion in the oral cavity.

The image capturing system 1 according to the present disclosure is used to output a subject image obtained by capturing an image of, as an example, the pharynx of the oral cavity. Accordingly, hereinafter, a case where a subject image of the pharynx is output by using the image capturing system 1 will be described. Furthermore, it is natural that the image capturing system 1 do not only output the subject image, but can also be used to capture an image of, for example, the pharynx of the oral cavity and determine a probability of a target person having influenza. The determination of the probability of having influenza is an example, and it is natural that the image capturing system 1 can be suitably used to determine any diseases that cause a difference in observations in the oral cavity. Examples of such a disease include streptococcal infection, adenovirus infection, EB virus infection, *mycoplasma* infection, hypertension, and the like.

In the present disclosure, the terms "determination", "diagnosis", and the like of a disease are used, but these terms do not necessarily mean definitive determination or diagnosis made by a physician. For example, the terms can naturally include a situation where a target person to be imaged himself or herself or a user other than a physician uses the image capturing system 1 according to the present disclosure to cause a processing device 100 included in the image capturing system 1 to make determination or diagnosis, or a situation where a physician is supported in making definitive determination or diagnosis.

FIG. 1 is a diagram illustrating a use state of the image capturing system 1 according to an embodiment of the present disclosure. Specifically, FIG. 1 is a diagram illustrating a use state of an image capturing device 200 in the image capturing system 1 according to the present disclosure. As illustrated in FIG. 1, a user inserts the image capturing device 200 into an auxiliary tool 300 in such a way that the image capturing device 200 is covered with the auxiliary tool 300, and inserts the image capturing device 200 that has been inserted into the auxiliary tool 300, into an oral cavity 712 of a target person. Accordingly, the image capturing device 200 is used to capture an image of an inside of the oral cavity 712. Specifically, first, a user (a target person 700 in some cases, or a person other than the target person 700 in other cases) inserts the image capturing device 200 into the auxiliary tool 300 from a leading end of the image capturing device 200. Then, in a state where the image capturing device 200 is covered with the auxiliary tool 300, the image capturing device 200 is inserted into the oral cavity 712. In this case, a leading end of the auxiliary tool 300 passes through an incisor 711, and is inserted to the vicinity of a soft palate 713. Then, in a state where the auxiliary tool 300 has been inserted into the oral cavity 712, the image capturing device 200 is inserted into the auxiliary tool 300 from the leading end of the image capturing device 200. Stated another way, the image capturing device 200 passes through the incisor 711, and is inserted to the vicinity of the soft palate 713. In this case, the auxiliary tool 300 (serving as a tongue depressor) pushes a tongue 714 downward, and restricts a movement of the tongue 714. Then, a satisfactory field of view of the image capturing device 200 is secured, and an image of a pharynx 715 that is located in front of the image capturing device 200 is captured.

A subject image (an image of the pharynx 715) that has been captured is transmitted from the image capturing device 200 to the processing device 100 that is communicably connected in a wired or wireless manner. A processor of the processing device 100 that has received the subject image processes a program stored in a memory of the processing device 100 to determine a probability of having influenza on the basis of the subject image. Then, a result is output to a display or the like.

Figure 2:
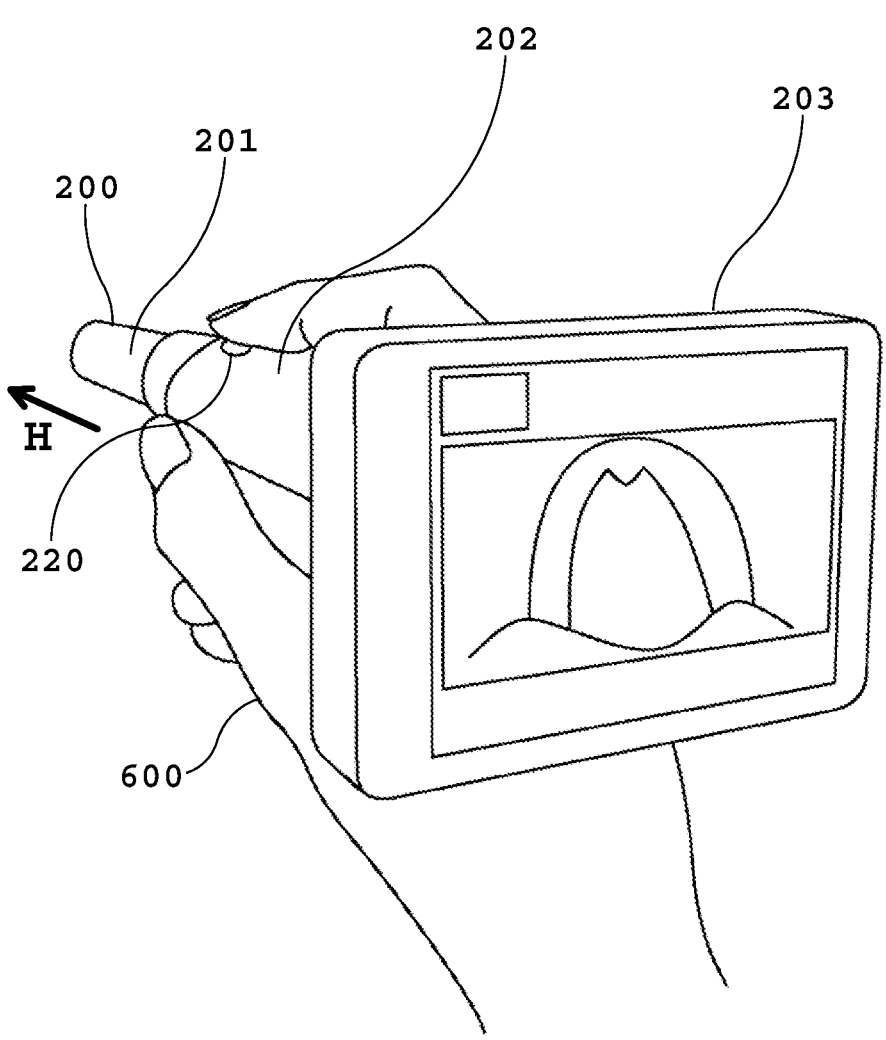
FIG. 2 is a diagram illustrating a use state of the image capturing system 1 according to the embodiment of the present disclosure.

Here, FIG. 2 is a diagram illustrating a use state of the image capturing system 1 according to the embodiment of the present disclosure. Specifically, FIG. 2 is a diagram illustrating a state where a user 600 has grasped the image capturing device 200 in the image capturing system 1. As illustrated in FIG. 2, the image capturing device 200 includes a main body 201, a grip 202, and a display 203 in order of insertion into the oral cavity. The main body 201 and the grip 202 are formed in an approximately columnar shape having a prescribed length along an insertion direction H into the oral cavity. Furthermore, the display 203 is disposed on a side opposite to a side of the main body 201 of the grip 202. Therefore, the image capturing device 200 is formed in an approximately columnar shape as a whole, and as illustrated in FIG. 2, the user 600 grasps the image capturing device 200 as if the user 600 grasps a pencil. Stated another way, in the use state, a display panel of the display 203 faces the user 600 himself or herself, and therefore the image capturing device 200 can be easily handled in a state where a subject image captured by the image capturing device 200 is being checked in real time.

Furthermore, when the user 600 grasps the grip 202 in an orientation where the subject image is displayed on the display 203 in an ordinary orientation, an image capturing button 220 is disposed on an upper face side of the grip. Therefore, when the user 600 has grasped the grip 202, the user 600 can easily press the image capturing button 220 by using the forefinger or the like.

Note that in the present disclosure, the subject image may be a moving image or a still image. As an example of an operation, if a power button is pressed, a camera captures a through image, and the captured through image is displayed on the display 203. Then, if the user presses the image capturing button, the camera captures one or more still images, and the captured images are displayed on the display 203. Alternatively, if the user presses the image capturing button, a moving image starts to be captured, and an image that is being captured by the camera is displayed on the display 203. Then, if the image capturing button is pressed again, capturing of the moving image is finished. As described above, in a series of operations, various images, such as a through image, a still image, or a moving image, are captured by the camera, and are displayed on the display. However, the subject image does not only mean a specified image of these images, but can include all of the images captured by the camera.

2. Configuration of Image Capturing System 1

Figure 3:
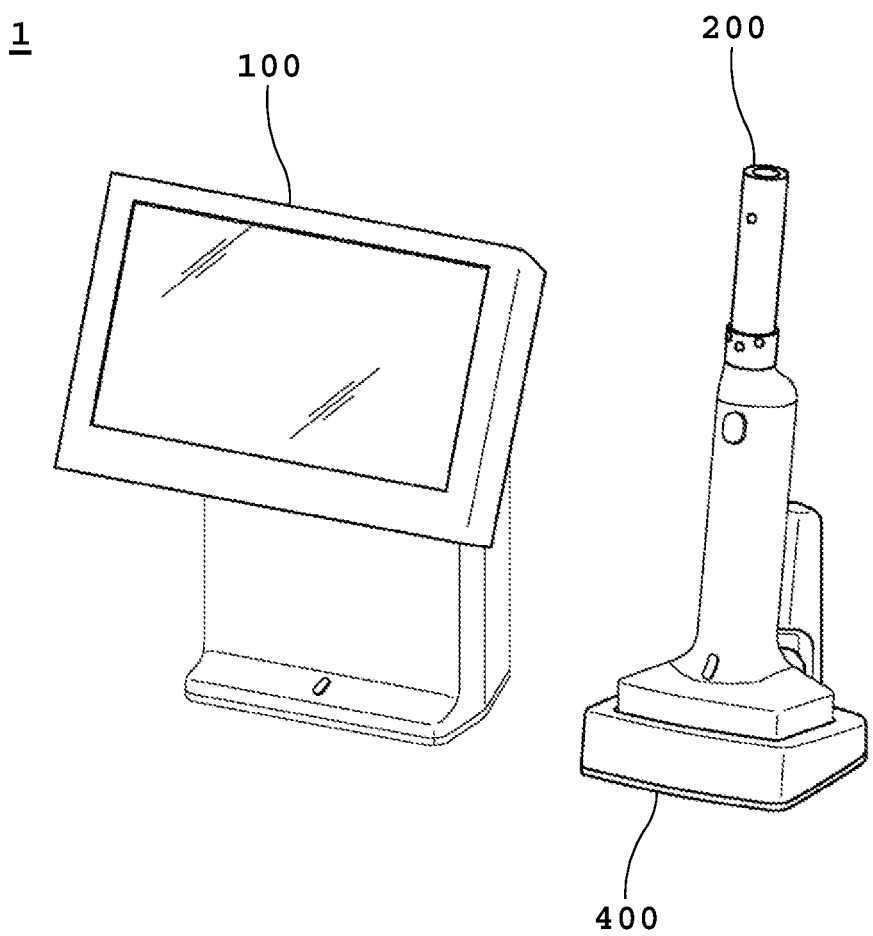
FIG. 3 is a schematic diagram of the image capturing system 1 according to the embodiment of the present disclosure.

FIG. 3 is a schematic diagram of the image capturing system 1 according to the embodiment of the present disclosure. As illustrated in FIG. 3, the image capturing system 1 includes the processing device 100, and the image capturing device 200 that is communicably connected to the processing device 100 in a wired or wireless manner. The processing device 100 receives an operation input performed by a user, and controls image capturing performed by the image capturing device 200. The processing device 100 also processes a subject image captured by the image capturing device 200, and outputs a processed image to the user, a target person, or the like.

At least the leading end of the image capturing device 200 is inserted into an oral cavity of the target person, and the image capturing device 200 captures an image of an inside of the oral cavity and in particular, the pharynx. Details of image capturing processing will be described later. A captured subject image is transmitted to the processing device 100 via a wired cable or wireless communication.

Note that the image capturing system 1 can further include a placing table 400, as needed. The image capturing device 200 can be stably placed on the placing table 400. Furthermore, the placing table 400 is connected to a power supply via the wired cable, and this enables power to be supplied from a power supply terminal of the placing table 400 through a power supply port of the image capturing device 200 to the image capturing device 200.

Figure 4:
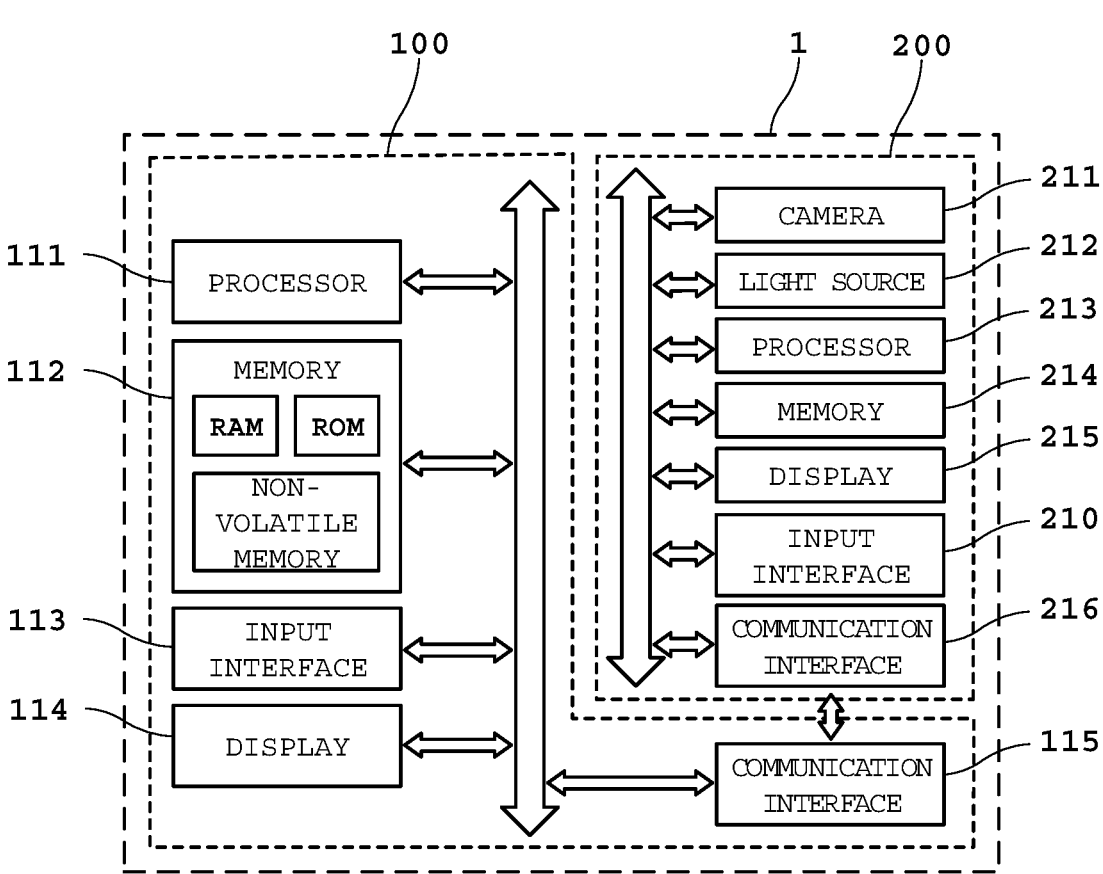
FIG. 4 is a block diagram illustrating a configuration of the image capturing system 1 according to the embodiment of the present disclosure.

FIG. 4 is a block diagram illustrating a configuration of the image capturing system 1 according to the embodiment of the present disclosure. As illustrated in FIG. 4, the image capturing system 1 includes the processing device 100 including a processor 111, a memory 112, an input interface 113, a display 114, and a communication interface 115, and the image capturing device 200 including a camera 211, a light source 212, a processor 213, a memory 214, a display panel 215, an input interface 210, and a communication interface 216. These respective components are electrically connected to each other via a control line and a data line. Note that the image capturing system 1 does not include all of the components illustrated in FIG. 3, and some components can be omitted, or another component can be added. For example, the image capturing system 1 can include a battery or the like that drives the respective components.

The processor 111 functions as a control unit that controls another component of the image capturing system 1 on the basis of a program stored in the memory 112. The processor 111 controls the driving of the camera 211 and the driving of the light source 212 on the basis of the program stored in the memory 112. The processor 111 also stores a subject image received from the image capturing device 200 in the memory 112, and processes the stored subject image. Specifically, the processor 111 receives an instruction input performed by a user on the input interface 113, and performs, on the basis of the program stored in the memory 112, processing for turning on the light source 212, and providing an instruction to capture an image by using the camera 211, processing for extracting, from a captured image, a still image to be used to determine disease likelihood, processing for performing prescribed processing on the extracted image to determine prescribed disease likelihood, processing for outputting the captured image or a determination result on the display 114, or the like, or other processing. The processor 111 is principally constituted by one or more CPUs, but a GPU or the like may be appropriately combined.

The memory 112 is constituted by a RAM, a ROM, a non-volatile memory, an HDD, or the like, and functions as a storage unit. The memory 112 stores, as a program, an instruction command for performing various types of control on the image capturing system 1 according to the present embodiment. Specifically, the memory 112 receives an instruction input performed by the user on the input interface 113, and stores a program for causing the processor 111 to perform processing for turning on the light source 212, and providing an instruction to capture an image by using the camera 211, processing for extracting, from a captured image, a still image to be used to determine disease likelihood, processing for performing prescribed processing on the extracted image to determine prescribed disease likelihood, processing for outputting the captured image or a determination result on the display 114, or the like, or other processing. Furthermore, the memory 112 stores a subject image captured by the camera 211 of the image capturing device 200, a result of determining disease likelihood by using the processor 111, various types of information relating to a target person including the target person 700, or the like, in addition to the program.

Note that in the present embodiment, the processor 111 determines likelihood of disease such as influenza from the captured image. In specific processing relating to this determination, as an example, many images that have been added with a label indicating the presence or absence of influenza infection, the many images including an image indicating the pharynx of a patient having influenza, are generated as training data, and machine learning is performed to generate a determination algorithm. Then, an image captured by the image capturing device 200 is applied to the determination algorithm, and therefore a probability of having influenza is quantified (for example, "98.5%"), and is indicated. The probability is not limited to a specific numerical value, and may be indicated, for example, in appropriate combination with determination of "positive" or "negative", evaluation of a level such as high, middle, or low, or the like.

The input interface 113 functions as an input unit that receives an instruction input performed by the user on the processing device 100 and the image capturing device 200. Examples of the input interface 113 include a "record button" for providing an instruction to start or finish video recording by using the image capturing device 200, a "confirm button" for performing various types of selection, a "return/cancel button" for returning to a previous screen or canceling a confirmation operation that has been input, a D-pad button for moving an icon or the like that is displayed on the display 114, an ON/OFF key for turning on or off a power supply of the processing device 100, and the like. Note that these various button keys may be physically prepared, as described as the various buttons described above, as described above, or may be displayed as icons on the display 114, and may be able to be selected by using a mouse, a keyboard, or the like serving as the input interface 113. Furthermore, as the input interface 113, a touch panel that is provided to be superimposed onto the display 114 and includes an input coordinate system that corresponds to a display coordinate system of the display 114 can be used, but this is not particularly illustrated. A scheme for detecting an instruction input performed by the user by using the touch panel may be any scheme such as electrostatic capacitance type or a resistive film type. Note that an operation input performed on the image capturing device 200 does not always need to be performed by using the input interface 113 of the processing device 100. The operation input can be performed by using an input interface included in the image capturing device 200.

The display 114 functions as a display unit that displays a subject image captured by the image capturing device 200. The display 114 is constituted by a liquid crystal panel, but is not limited to the liquid crystal panel, and may be constituted by an organic EL display, a plasma display, or the like.

The communication interface 115 functions as a communication unit that transmits or receives information to/from the image capturing device 200 and/or another device. Examples of information to be transmitted or received include various commands for providing an instruction to, for example, start image capturing, terminate image capturing, or transfer a subject image or information relating to a target person that is transmitted to the image capturing device 200, a subject image received from the image capturing device 200, and the like. Examples of the communication interface 115, as described above, include various terminals for wired communication including a terminal for serial communication, such as a USB, a terminal for parallel communication, such as IEEE 1284, and the like. Furthermore, in addition to or instead of such a terminal for wired communication, a wireless communication interface that employs a broadband wireless communication scheme represented by the LTE scheme, or a scheme relating to a narrowband wireless communication such as a wireless LAN represented by IEEE 802.11 or Bluetooth (registered trademark) can be provided.

The camera 211 is driven according to an instruction from the processing device 100, and functions as an image capturing unit that detects reflected light that has been reflected on the oral cavity serving as a subject, and generates a subject image. The camera 211 includes, as an example, a CMOS image sensor, and a lens system and a driving system for achieving desired functions in order to detect the light. An image sensor is not limited to the CMOS image sensor, and another sensor such as a CCD image sensor can be used. The camera 211 can have an autofocus function, but this is not particularly illustrated. It is preferable that the camera 211 be set, for example, in such a way that a specified portion is in focus on a front surface of a lens. The camera 211 can also have a zoom function, and it is preferable that the camera 211 be set to capture an image at an appropriate magnification according to a size of the pharynx or an influenza follicle.

Here, it is known that a lymph follicle that appears in a deepest portion of the pharynx in the oral cavity has a pattern peculiar to influenza. This lymph follicle having the peculiar pattern is called an influenza follicle, and is a sign characteristic of influenza, and it is considered that the lymph follicle appears in about two hours after appearance of symptoms. As described above, the image capturing system 1 according to the present embodiment can also be used to capture an image of, for example, the pharynx of the oral cavity and detect the follicle described above to determine a probability of a target person having influenza. Stated another way, in the present embodiment, the camera 211 is inserted into the oral cavity of a target person, and is used to capture an image of the pharynx that is located in a deep portion of the oral cavity, and therefore a distance between the camera 211 and a subject is relatively close. Accordingly, the camera 211 has an angle of view (2θ) that causes a value calculated according to [(distance from leading end portion of camera 211 to posterior wall of pharynx)*tan θ] to be 20 mm or more (vertically) and 40 mm or more (horizontally). By using a camera having such an angle of view, even if the camera 211 and the subject are close to each other, a wider range can be imaged. Accordingly, as the camera 211, a normal camera can be used, and what is called a wide angle camera or a super-wide angle camera can also be used.

Furthermore, in the present embodiment, a subject that is imaged by the camera 211 is principally the pharynx or an influenza follicle that is formed in a pharynx portion. In general, the pharynx is formed in a depth direction, and therefore if a depth of field is small, an anterior pharynx and a posterior pharynx are out of focus, and it is difficult to obtain an appropriate subject image to be used for determination performed by the processing device 100. Accordingly, the camera 211 has at least a depth of view of 20 mm or more, and preferably, a depth of view of 30 mm or more. By using a camera having such a depth of view, a subject image in which any portion from the anterior pharynx to the posterior pharynx is in focus can be obtained.

The light source 212 is driven according to an instruction from the processing device 100 or the image capturing device 200, and functions as a light source unit that applies light into the oral cavity. The light source 212 includes one or more light sources. In the present embodiment, the light source 212 is constituted by one or more LEDs, and each of the LEDs applies light having a prescribed frequency band toward the oral cavity. As the light source 212, light having a desired band of an ultraviolet band, a visible light band, and an infrared light band, or a combination thereof is used. Note that in a case where the processing device 100 determines disease likelihood of influenza or the like, it is preferable that light having a short wavelength band of the ultraviolet light band be used. Application of light having this band to the influenza follicle causes a specified component of the influenza follicle to react, and therefore there is a possibility that disease likelihood can be more reliably determined.

The processor 213 functions as a control unit that controls another component of the image capturing device 200 on the basis of a program stored in the memory 214. The processor 213 performs control to drive the camera 211 and drive the light source 212 on the basis of the program stored in the memory 214, and also performs control to store a subject image captured by the camera 211 in the memory 214. The processor 213 also performs control to output, to the display 203, a subject image or information relating to a target person that is stored in the memory 214, or transmit the subject image or the information to the processing device 100. The processor 213 is principally constituted by one or more CPUs, but may be appropriately combined with another processor.

The memory 214 is constituted by a RAM, a ROM, a non-volatile memory, an HDD, or the like, and functions as a storage unit. The memory 214 stores, as a program, an instruction command for performing various types of control on the image capturing device 200. Furthermore, the memory 214 stores a subject image captured by the camera 211, various types of information relating to a target person including the target person 700, or the like, in addition to the program.

The display panel 215 functions as a display unit that is provided in the display 203, and displays a subject image captured by the image capturing device 200. The display panel 215 is constituted by a liquid crystal panel, but is not limited to the liquid crystal panel, and may be constituted by an organic EL display, a plasma display, or the like.

The input interface 210 functions as an input unit that receives an instruction input performed by the user on the processing device 100 and the image capturing device 200. Examples of the input interface 210 include a "record button" for providing an instruction to start or finish video recording by using the image capturing device 200, a "power button" for turning on or off a power supply of the image capturing device 200, a "confirm button" for performing various types of selection, a "return/cancel button" for returning to a previous screen or canceling a confirmation operation that has been input, a D-pad button for moving an icon or the like that is displayed on the display 114, and the like. Note that these various button keys may be physically prepared, or may be displayed as icons on the display 215, and may be able to be selected by using a touch panel or the like that is disposed as the input interface 210 to be superimposed onto the display 215. A scheme for detecting an instruction input performed by the user by using the touch panel may be any scheme such as electrostatic capacitance type or a resistive film type.

The communication interface 216 functions as a communication unit that transmits or receives information to/from the image capturing device 200 and/or another device. Examples of information to be transmitted or received include various commands for providing an instruction to, for example, start image capturing, terminate image capturing, or transfer a subject image or information relating to a target person that is received from the image capturing device 200, a subject image transmitted to the image capturing device 200, and the like. The communication interface 115, as described above, is provided to correspond to a communication interface of the processing device 100, and examples include various terminals for wired communication including a terminal for serial communication, such as a USB, a terminal for parallel communication, such as IEEE 1284, and the like. Furthermore, in addition to or instead of such a terminal for wired communication, a wireless communication interface that employs a broadband wireless communication scheme represented by the LTE scheme, or a scheme relating to a narrowband wireless communication such as a wireless LAN represented by IEEE 802.11 or Bluetooth (registered trademark) can be provided.

3. Configuration of Image Capturing Device 200

Figure 5:
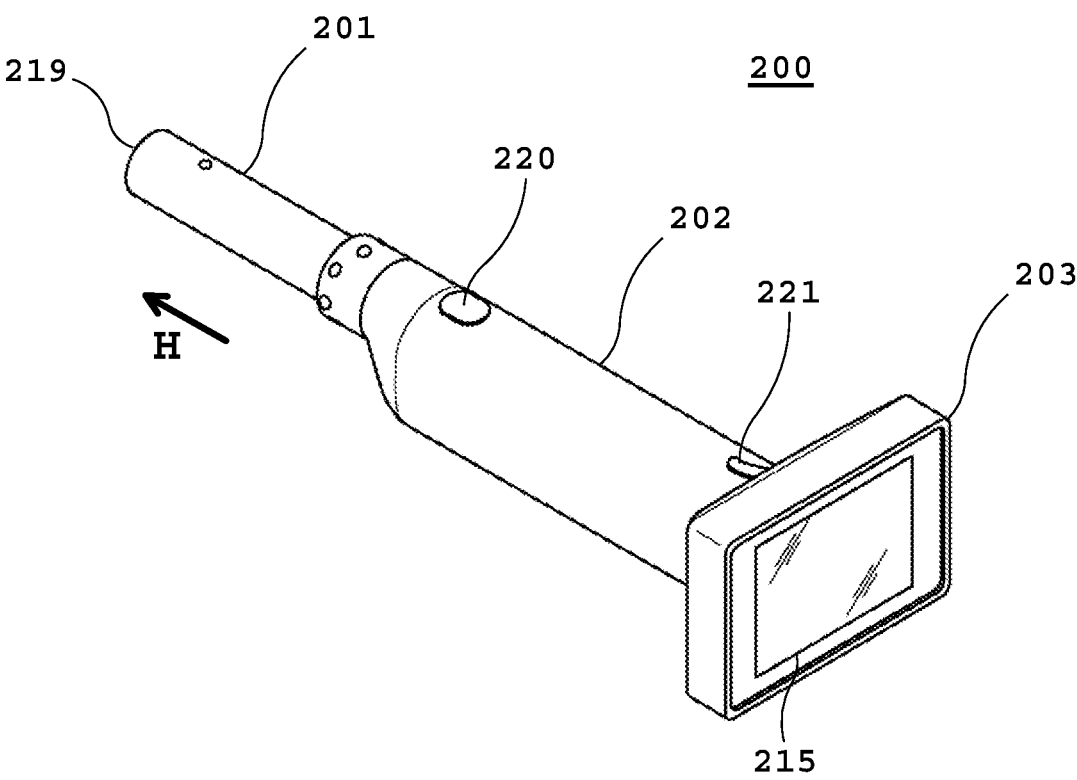
FIG. 5 is a perspective view illustrating a configuration of an image capturing device 200 according to the embodiment of the present disclosure.

The image capturing system 1 according to the present disclosure includes the image capturing device 200 that captures an image to be processed by the processing device 100. FIG. 5 is a perspective view illustrating a configuration of the image capturing device 200 according to the embodiment of the present disclosure. As illustrated in FIG. 5, the image capturing device 200 includes the main body 201 that houses the camera 211, and can guide light applied from the light source 212 to an inside, a grip 202 that is connected to a base end of the main body 201, and is grasped by a user, a diffusion plate 219 that is disposed at a leading end of the main body 201, and the display 203 that is connected to a base end of the grip 202, and can output a subject image captured by the camera 211.

On an upper face side of the grip 202, an image capturing button 220 that is pressed by a user 600 with the finger to provide an instruction to start or terminal capturing of an image of a subject, and a power button 221 for providing an instruction to turn on or off the power supply of the image capturing device 200. Stated another way, starting or terminating image capturing by using the image capturing device 200 or turning on or off the power supply is controlled according to an instruction received from the processing device 100 in some cases, and is controlled according to the pressing of these buttons of the image capturing device 200 in other cases.

Figure 6A:
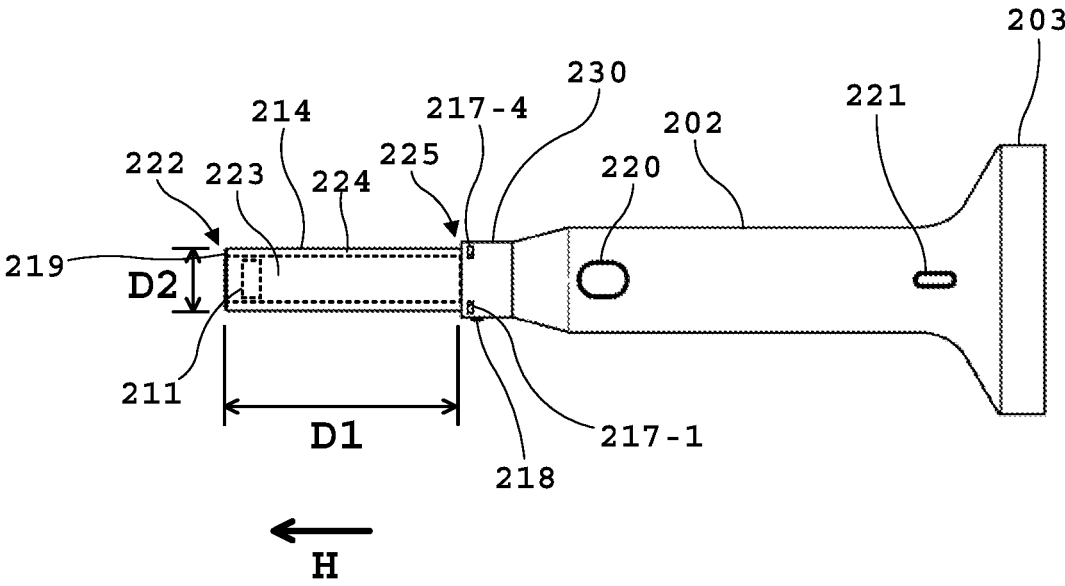
FIG. 6A is a top view illustrating the configuration of the image capturing device 200 according to the embodiment of the present disclosure.
Figure 6B:
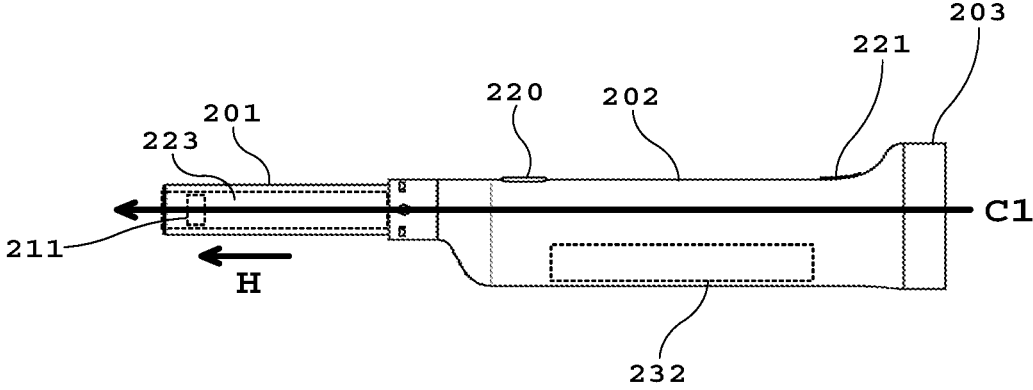
FIG. 6B is a side view illustrating the configuration of the image capturing device 200 according to the embodiment of the present disclosure.
Figure 6C:
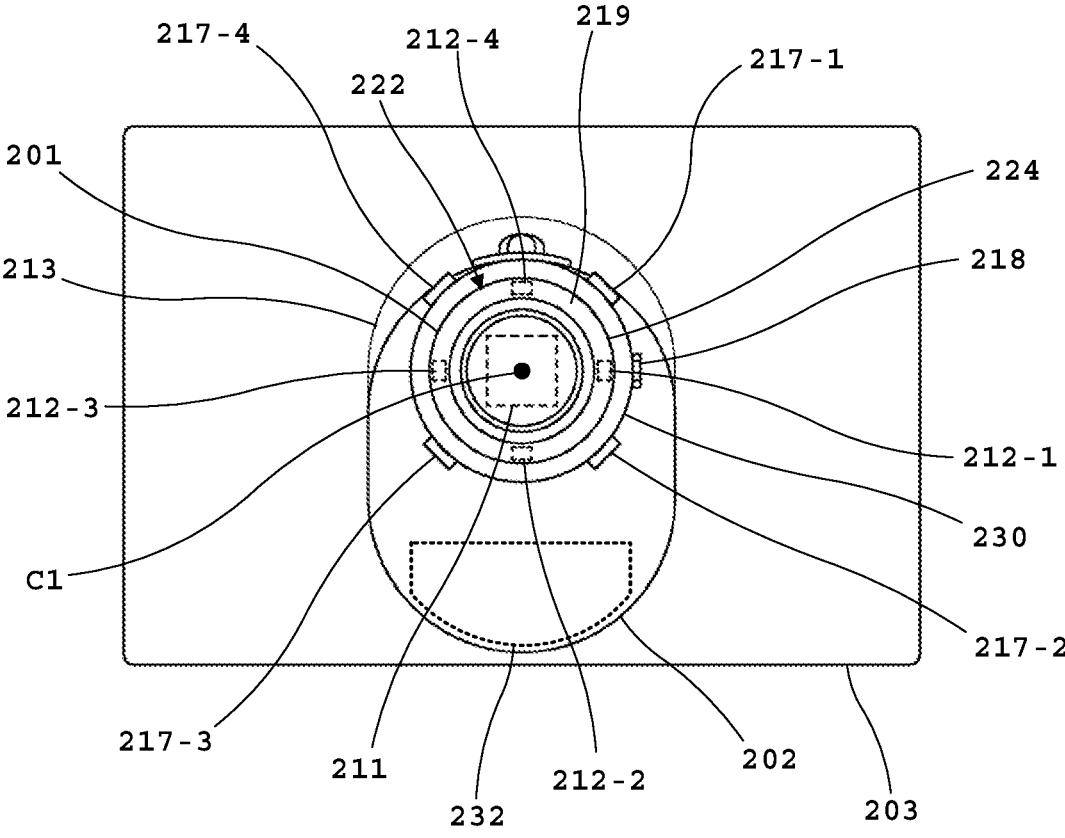
FIG. 6C is a front view illustrating the configuration of the image capturing device 200 according to the embodiment of the present disclosure.
Figure 6D:
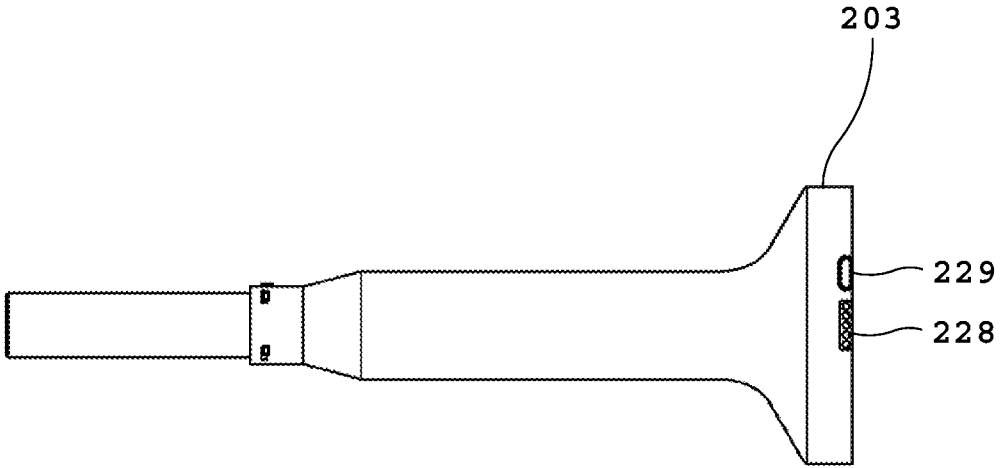
FIG. 6D is a bottom view illustrating the configuration of the image capturing device 200 according to the embodiment of the present disclosure.

FIG. 6A is a top view illustrating the configuration of the image capturing device 200 according to the embodiment of the present disclosure. FIG. 6B is a side view illustrating the configuration of the image capturing device 200 according to the embodiment of the present disclosure. FIG. 6C is a front view illustrating the configuration of the image capturing device 200 according to the embodiment of the present disclosure. FIG. 6D is a bottom view illustrating the configuration of the image capturing device 200 according to the embodiment of the present disclosure. A specific configuration of the image capturing device 200 is described below with reference to FIGS. 6A to 6D.

As illustrated in FIG. 6A, the main body 201 includes a base end 225 and a leading end 222, and is constituted by a columnar body having a prescribed length in a direction in which light is applied from the light source 212, that is, a direction that is approximately parallel to a direction H of insertion into an oral cavity. At least the leading end 222 of the main body 201 is inserted into the oral cavity.

The main body 201 is formed in a columnar shape that is a hollow cylindrical shape having a perfect-circle cross section. A wall 224 of the main body 201 can be obtained by using any material that can guide light to an inside, and, as an example, a thermoplastic resin. As the thermoplastic resin, polyolefin resin such as chain polyolefin resin (polypropylene resin or the like) or cyclic polyolefin resin (norbornene resin or the like), cellulose ester resin such as triacetyl cellulose or diacetyl cellulose, polyester resin, polycarbonate resin, (meth)acrylic resin, polystyrene resin, a mixture or copolymer thereof, or the like is used. Stated another way, the wall 224 of the main body 201 functions as a light guide that guides light applied from the light source into the oral cavity or toward the diffusion plate.

The main body 201 is formed to be hollow, and therefore the wall 224 forms a housing space 223 inside the wall 224. This housing space 223 houses the camera 211. Note that it is sufficient if the main body 201 is formed in a columnar shape including the housing space 223. Accordingly, the housing space 223 does not need to have a cylindrical shape having a perfect-circle cross section, and a cross section may be an ellipse or a polygon. Furthermore, the main body 201 does not always need to be formed to have a hollow internal portion.

Here, a length of the main body 201 is determined, as an example, depending on a positional relationship with an incisor of a target person. In general, in the target person, an oral cavity is formed from the incisor toward a deep side of the throat, and a pharynx serving as a subject is located in a deepest portion. Accordingly, a leading end of the image capturing device 200 needs to be inserted to the vicinity of a soft palate in order to capture an image of the pharynx. The target person has a distance d1 from the incisor to the soft palate. This distance d1 is generally about 70 100 mm to 200100 mm according to Nobuo OHYA, M. D., "Pharyngeal Cross-sectional Area in Sleep Apnea Syndrome," J. Jpn. Bronchoesophagol. Soc., Vol. 40, No. 5, pp. 396-402.

Return to FIG. 6A. In the present embodiment, the main body 201 has a distance D1 as a length from the leading end 222 to the base end 225. This distance D1 is 0% to 90% or less, and preferably, 5% to 80% or less, of the distance d1 from the incisor to the soft palate. In general, the insertion of a foreign material into the deep side of the throat causes a feeling of vomiting. On the other hand, if the main body 201 is short, a distance between the camera 211 and the subject is too long. The distance D1 described above can avoid a feeling of vomiting, and a distance to the subject can be appropriately kept.

A leading end of the grip 202 is connected to the base end 225 of the main body 201. A user grasps the grip 202, and performs, for example, an operation to extract or insert the image capturing device 200. The grip 202 is constituted by a columnar body having a prescribed length in a direction that is approximately parallel to the direction H of insertion into the oral cavity, that is, along a longitudinal direction of the main body 201, and the grip 202 and the main body 201 are disposed on the same straight line in the direction H. Note that in the present embodiment, the grip 202 is formed in such a way that a vertical cross section is an approximately oval shape, but the vertical cross section does not need to be an oval shape, and may be a perfect circle, an ellipse, or a polygon.

Here, a width (a distance D2) of the main body 201 in a direction that is perpendicular to a direction that connects the leading end 222 and the base end 225 of the main body 201 is determined depending on, as an example, a relationship with an open width in an upward/downward direction of the mouth of the target person. The target person has a distance d2 as the open width in the upward/downward direction of the mouth. An average of the distance d2 is 3.5 cm to 4.0 cm in the case of a general adult male, according to Hiroyasu TSUKAHARA, et. al., "A statistical evaluation of normal maximal mouth opening of Japanese adults," Japanese Society of Oral and Maxillofacial Surgeons, Vo. 44, No. 2, pp. 159-167.

The image capturing device 200 according to the present embodiment is inserted together with an auxiliary tool 300 into a width of this distance d2, and the user captures images while observing an inside of the oral cavity from a clearance obtained by inserting the image capturing device 200 and the auxiliary tool 300 in some cases. Therefore, it is useful to not disturb the visibility of the user in a state where the image capturing device 200 has been inserted. Accordingly, the distance D2 of the main body 201 is a width of 80% or less, and preferably, 60% or less, of the distance d2 serving as the open width in the upward/downward direction of the mouth, or is 3.2 cm or less, and preferably, 2.4 cm or less.

The grip 202 includes a coupling portion 230 in a position closest to the base end 225 of the main body 201, and is coupled to the main body 201 by using the coupling portion 230. On an outer periphery of the coupling portion 230, engagement projections 217 (217-1 to 217-4) and a positioning projection 218 that are used to position the auxiliary tool 300 are disposed. The engagement projections 217 are mutually engaged with engagement projections 318 (318-1 to 318-4) that are provided in the auxiliary tool 300. Furthermore, the positioning projection 218 is inserted into an insertion hole 321 that is provided in the auxiliary tool 300, and causes the image capturing device 200 and the auxiliary tool 300 to be mutually positioned. Note that in the present embodiment, as the engagement projections 217 of the main body 201, four engagement projections (the engagement projections 217-1 to 217-4) in total are disposed at equal intervals on a surface of the grip 202 in positions near the base end 225 of the main body 201. Furthermore, as the positioning projection 218, a single positioning projection is disposed between the engagement projections 217 on the surface of the grip 202 in a position near the base end 225 of the main body 201. However, this is not restrictive, and either the engagement projections 217 or the positioning projection 218 may be disposed. Furthermore, any number of engagement projections 217 or positioning projections 218 may be disposed, if one or more engagement projections 217 or positioning projections 218 are disposed.

Furthermore, the grip 202 includes the image capturing button 220 in a position near the base end 225 of the main body 201 on an upper face of the grip 202, that is, near a leading end in the direction H of insertion into the oral cavity of the grip 202. Therefore, when the user 600 has grasped the grip 202, the user 600 can easily press the image capturing button 220 by using the forefinger or the like. Furthermore, the grip 202 includes the power button 221 in a position near the display 203 on the upper face of the grip 202, that is, in a position on a side opposite to the image capturing button 220 of the grip 202. This can avoid a situation where the power button 221 is erroneously pressed while the user 600 is grasping the grip 202, and is capturing images.

The display 203 has an approximately rectangular parallelepiped shape as a whole, and the display 203 and the main body 201 are disposed on the same straight line in the direction H. Furthermore, the display 203 includes a display panel on a face in a direction opposite to the direction H of insertion into the oral cavity (that is, a direction toward the user). Accordingly, the display 203 is formed in such a way that a face including the display panel is approximately perpendicular to a longitudinal direction of the main body 201 and the grip 202 that are formed to be approximately parallel to the direction H of insertion into the oral cavity. The display 203 is coupled to the grip 202 on a side opposite to the oral cavity in the grip 202 on a face that faces the face including the display panel. Note that a shape of the display is not limited to an approximately rectangular parallelepiped shape, and may be any shape such as a cylindrical shape.

Here, the image capturing device 200 can be placed in a vertical direction in such a way that the face including the display panel is in contact with a placing surface. Therefore, at least an outer periphery of the face including the display panel of the display 203 is formed on a rough plane that is suitable for placement.

The diffusion plate 219 is disposed at the leading end 222 of the main body 201, and diffuses, toward the inside of the oral cavity, light that has been applied from the light source 212 and has passed through the main body 201. The diffusion plate 219 has a shape that corresponds to a sectional shape of a portion that can guide light in the main body 201. In the present embodiment, the main body 201 is formed in a hollow cylindrical shape. Accordingly, a cross section of the diffusion plate 219 is also hollow in accordance with the shape of the main body 201.

The camera 211 is used to detect reflected light that has been diffused from the diffusion plate 219, has been applied into the oral cavity, and has been reflected on a subject, and generate a subject image. The camera 211 is disposed inside the wall 224 of the main body 201, that is, in the housing space 223 that is formed inside the main body 201 in such a way that the camera 211 and the main body 201 are located on the same straight line in the direction H. Note that in the present embodiment, only a single camera 211 has been described, but the image capturing device 200 may include a plurality of cameras. By generating a subject image by using the plurality of cameras, the subject image includes information relating to a stereoscopic shape. Furthermore, in the present embodiment, the camera 211 is disposed in the housing space 223 of the main body 201, but may be disposed at the leading end 222 of the main body 201 or in the main body 201 (this may be an inside of the main body 201 or an outer periphery of the main body 201).

As illustrated in FIG. 6B, in a side view, the main body 201, the grip 202, the display 203, and the camera 211 are disposed on the same straight line along the direction H of insertion into the oral cavity. As described with reference to FIG. 6A, the image capturing button 220 and the power button 221 are disposed on an upper face at a time when the image capturing device 200 is placed in a horizontal direction in a state where a subject image is displayed in an ordinal orientation on the display 203.

The grip 202 houses a battery serving as a power supply for driving each element of the image capturing device 200. Specifically, the grip 202 includes a housing space 232 for housing the battery, and can house the battery in the housing space 232. Here, the image capturing device 200 has a center axis Cl along a longitudinal direction of the main body 201 that is formed in an approximately cylindrical shape (that is, the direction H of insertion into the oral cavity). It is desirable that the housing space 232 of the battery be formed in such a way that at least part or the entirety of the housing space 232 is located below this center axis Cl when the image capturing device 200 is placed in the horizontal direction in a state where the subject image is displayed in an ordinary orientation on the display 203. As described above, the housing space 232 is located below the center axis Cl of the main body 201, and therefore the battery having a reasonable weight can be housed below the center axis Cl. This causes the center of gravity to be located on a lower side when a user has grasped the grip 202 of the image capturing device 200, and an operation can be performed more stably.

As illustrated in FIG. 6C, in a front view from a side of the leading end 222 of the main body 201, the grip 202 and the display 203 are disposed on a line along the center axis Cl of the main body 201 (in FIG. 6C, on a line in a depth direction). Furthermore, the camera 211 is disposed inside the main body 201 and on the line described above along the center axis Cl, and reflected light from the subject that has entered from the leading end of the main body 201 can be detected.

The main body 201 is formed in a hollow columnar shape in which the wall 224 has formed a longer side in a direction of insertion into the oral cavity (in FIG. 6C, the depth direction), and the diffusion plate 219 is provided at a forefront end of the wall 224. On the other hand, the light source 212 is provided at a rear end of the wall 224 (stated another way, on a side of the base end 225 of the main body 201), and light that has been applied from the light source 212 passes through the wall 224, and is applied from the diffusion plate 219 into the oral cavity.

On the side of the base end 225 (not illustrated) of the main body 201, the grip 202 is coupled by using the coupling portion 230. The coupling portion 230 is formed in a cylindrical shape similarly to the main body 201 in such a way that the coupling portion 230 is located along the outer periphery of the main body 201 having a cylindrical cross section. On an outer periphery of the coupling portion 230 that is formed in a cylindrical shape, the four engagement projections 217-1 to 217-4 are disposed at equal intervals, and the single positioning projection 218 is disposed. In FIG. 6C, four engagement projections and a single positioning projection are illustrated, but different numbers of engagement projections and positioning projections may be disposed.

In a from view from on a side of the leading end 222 of the main body 201, the housing space 232 is provided in the grip 202 in such a way that at least part or the entirety of the housing space 232 is located below the center axis Cl of the main body 201, and the housing space 232 houses the battery.

As illustrated in FIG. 6D, an input/output terminal 229 and a power supply port 228 are disposed on a side of a lower face at a time when the image capturing device 200 is placed in the horizontal direction in a state where the subject image is displayed in an ordinary orientation on the display 203. Stated another way, the input/output terminal 229 and the power supply port 228 are disposed on the same face of the outer periphery of the display 203. The disposition of both components on the same face, as described above, can avoid, for example, a situation where power is supplied from the input/output terminal 229 when the image capturing device 200 is placed on the placing table 400 and power is supplied via the power supply port 228.

4. Configuration of Auxiliary Tool 300

Figure 7A:
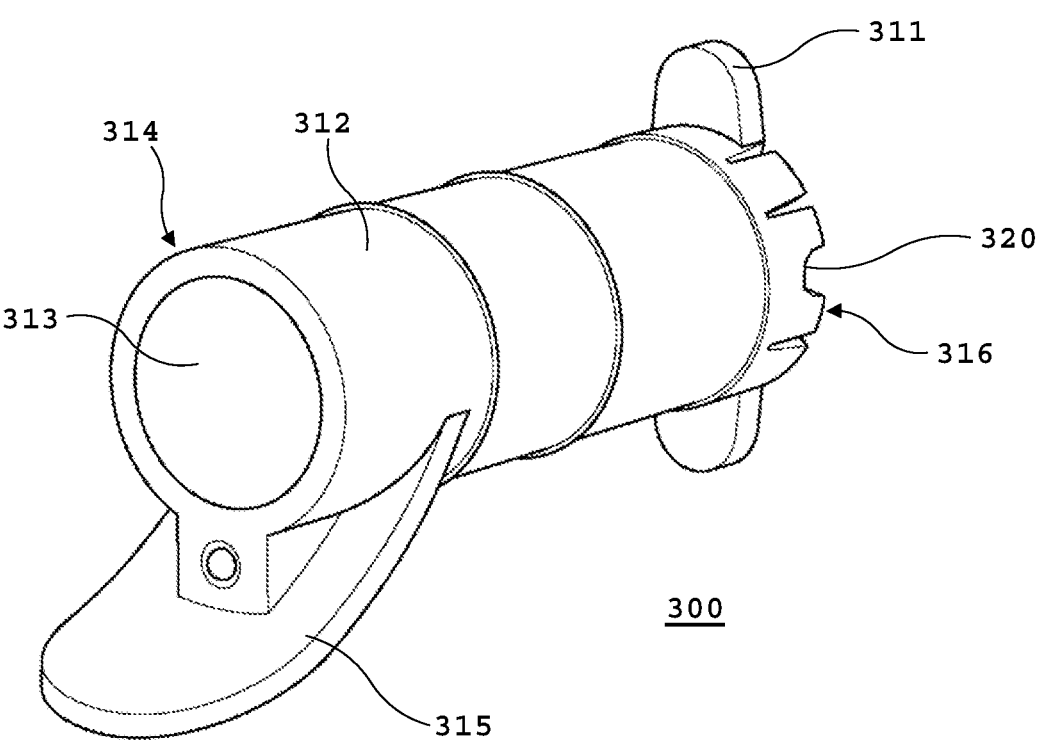
FIG. 7A is a perspective view illustrating a configuration of an auxiliary tool 300 according to the embodiment of the present disclosure.

FIG. 7A is a perspective view illustrating a configuration of the auxiliary tool 300 according to the embodiment of the present disclosure. The auxiliary tool 300 is an auxiliary tool that is used to capture images of the inside of the oral cavity of a target person. Accordingly, the auxiliary tool 300 is not always needed in a case where an image of the inside of the oral cavity is captured by using the image capturing device 200, and the auxiliary tool 300 may not be used in response to a desire of a user or a target person. At least a portion on a leading end side of the image capturing device 200 is inserted into the auxiliary tool 300. Accordingly, it is preferable that the auxiliary tool 300 have a light transmitting capability from a viewpoint of securing a satisfactory field of view without disturbing the image capturing device 200.

In the present embodiment, the auxiliary tool 300 is manufactured by using an integrally molded resin. However, the auxiliary tool 300 may be manufactured by using another material such as paper, cloth, or metal or a combination thereof. Furthermore, it is desirable that the auxiliary tool 300 be of a disposable type, but may be of a reusable type.

As illustrated in FIG. 7A, the auxiliary tool 300 includes a main body 312 that is formed in a tubular shape, a pair of grasping plates 311 that are disposed at a base end 316 of the main body 312, and a tongue depressor 315 that is disposed near a leading end 314 of the main body 312.

The main body 312 is configured to cover at least a portion on a side of the leading end 222 of the main body 201 of the image capturing device 200 inside the main body, and therefore that main body 312 is formed in a cylindrical shape having a prescribed length in accordance with a length of the main body 201. A base-end side opening 320 into which the image capturing device 200 is inserted is disposed on a side of the base end 316, and a leading-end side opening 313 that applied light from the light source 212 of the image capturing device 200 and reflected light from a subject pass through is disposed on a side of the leading end 314. Note that in the present embodiment, the auxiliary tool 300 is inserted into an oral cavity from the leading end 314.

Furthermore, in the present embodiment, the main body 201 of the image capturing device 200 has an internal diameter and an external diameter that are substantially constant from the base end 225 to the leading end 222. Accordingly, the main body 312 of the auxiliary tool 300 is also formed to have an internal diameter and an external diameter that are substantially constant in a longitudinal direction in accordance with this shape. Note that it is preferable that a sectional shape of the main body 312 be formed to correspond to a sectional shape of the main body 201 of the image capturing device 200, but any shape that enables insertion may be employed, and any shape such as a perfect circle, an ellipse, or a polygon may be employed.

The pair of grasping plates 311 are disposed along the base end 316 of the main body 312. The grasping plates 311 are used to be grasped with the hand when a user inserts the auxiliary tool 300 into the oral cavity of a target person. In the present embodiment, the grasping plates 311 function as a regulation member in which a face on a leading end side abuts onto a lip or the like of the target person when the auxiliary tool 300 is inserted into the oral cavity such that that further insertion of the auxiliary tool 300 is regulated. Note that in the present embodiment, the pair of grasping plates 311 are disposed on a side of the base end 316 of the main body 312 to be symmetrical in the upward/downward direction, but a grasping plate may be formed in a doughnut shape along the base end 316 of the main body 312, and any shape may be employed.

The tongue depressor 315 is disposed below the main body 312 (on a side toward a tongue in the oral cavity), and is formed on a blade toward the tongue. In capturing images by using the image capturing device 200, the tongue of a target person moves in front of the image capturing device 200, and this hinders capturing images of the inside of the oral cavity. The tongue depressor 315 pushes the tongue downward to restrict a movement of the tongue in the oral cavity, and prevents the tongue from being located in front of the image capturing device 200. Accordingly, in the present embodiment, the tongue depressor 315 is formed in a blade shape, but any shape may be employed if this function can be achieved.

Figure 7B:
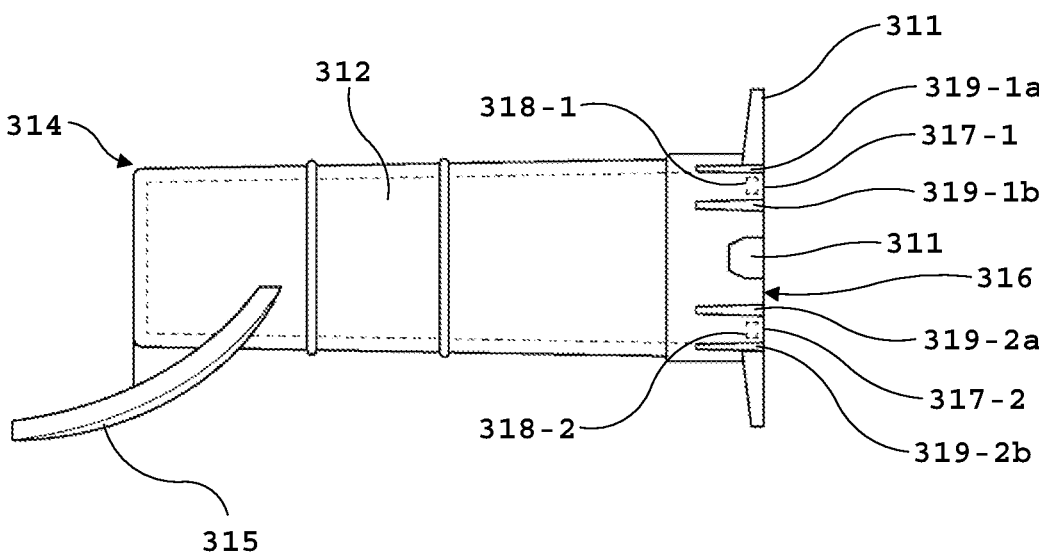
FIG. 7B is a side view illustrating a configuration of the auxiliary tool 300 according to the embodiment of the present disclosure.

FIG. 7B is a side illustrating an outline of a configuration of a side face of the auxiliary tool 300 according to the embodiment of the present disclosure. As illustrated in FIG. 7B, the auxiliary tool 300 includes the tongue depressor 315 near a side of the leading end 314 of the main body 312, and the grasping plates 311 on a side of the base end 316, as described above.

Furthermore, on a side of the base end 316 of the main body 312, a mechanism for positioning at a time when the image capturing device 200 is inserted from a side of the base end 316 is included. Specifically, the main body 312 includes a pair of grooves 319 that are formed to have a prescribed length in a direction perpendicular to an outer periphery of the main body 312, a piece 317 that is formed by these grooves, an engagement projection 318 that is disposed in each of the pieces 317, and is configured to engage with each of the engagement projections 217 that are disposed at a leading end of the grip 202 of the image capturing device 200, and an insertion hole 321 into which the positioning projection 218 of the grip 202 is inserted.

The engagement projection 318 is provided in a position that corresponds to each of the engagement projections 217 that are disposed in the grip 202 of the image capturing device 200 to project in an inward direction of the main body 312. Accordingly, in the present embodiment, four engagement projections 318-1 to 318-4 are disposed in positions that correspond to the four engagement projections 217-1 to 217-4. Furthermore, the insertion hole 321 is provided in a position that corresponds to the positioning projection 218 that is disposed in the grip 202 of the image capturing device 200. Accordingly, in the present embodiment, a single insertion hole 321 is disposed in a position that corresponds to a single positioning projection 218.

5. Use States of Image Capturing Device 200 and Auxiliary Tool 300

Figure 8:
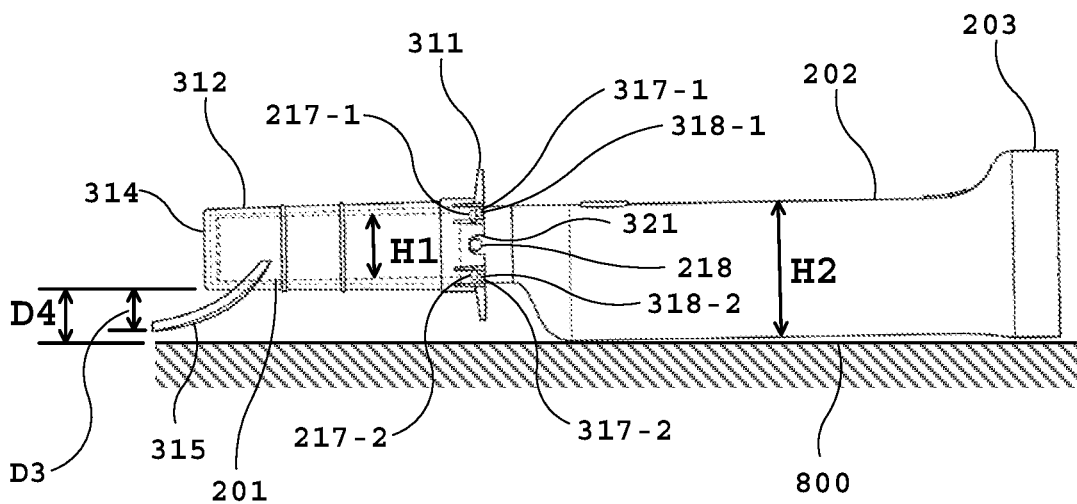
FIG. 8 is a schematic diagram illustrating use states of the image capturing device 200 and the auxiliary tool 300 according to the embodiment of the present disclosure.

FIG. 8 is a schematic diagram illustrating use states of the image capturing device 200 and the auxiliary tool 300 according to the embodiment of the present disclosure. Each mechanism that is disposed at the base end 316 of the main body 312 in FIG. 7B is described below with reference to FIG. 8. First, when the image capturing device 200 has been inserted into the base end 316 of the auxiliary tool 300, and has reached the vicinity of the leading end 314, the engagement projections 217 that are formed to project in an outward direction of the grip 202 of the image capturing device 200 abut onto the engagement projections 318 that are formed in an inward direction of the main body 312 of the auxiliary tool 300. Here, in the present embodiment, the engagement projections 318-1 to 318-4 of the main body 312 are formed in pieces 317-1 to 317-4 that are formed by the pairs of grooves 319-1a and 319-1b to 319-4a and 319-4b. Accordingly, if force has been further applied in a direction of insertion of the image capturing device 200 in a state where the engagement projections 217 of the image capturing device 200 abut onto the engagement projections 318 of the auxiliary tool 300, the pieces 317 formed by the pairs of grooves 319 are raised. This causes the engagement projections 217 of the image capturing device 200 to be further inserted beyond the engagement projections 318 of the auxiliary tool 300.

Next, if the image capturing device 200 has been inserted beyond the engagement projections 318 of the auxiliary tool 300, the positioning projection 218 that is provided to project in an outward direction on the grip 202 of the image capturing device 200 is inserted into the insertion hole 321 of the auxiliary tool 300. Then, the positioning projection 218 of the image capturing device 200 abuts onto a wall face of the insertion hole 321 that is formed on a side of the leading end 314. This regulates the further insertion of the image capturing device 200 toward the leading end 314 of the auxiliary tool 300.

Stated another way, in the present embodiment, in a state where the image capturing device 200 has been completely inserted into the auxiliary tool 300, a movement of the image capturing device 200 in a direction of insertion of the image capturing device 200 is regulated by the positioning projection 218 and the insertion hole 321, and a movement of the image capturing device 200 in a direction opposite to the direction described above, that is, a direction where the image capturing device 200 is detached is regulated by the engagement projections 217 and the engagement projections 318.

Here, FIG. 8 illustrates a case where the image capturing device 200 is placed on a placing surface 800 in a horizontal direction in a state where a subject image is displayed in an ordinal orientation on the display 203. In this case, as illustrated in FIG. 8, the main body 201 has a width H1 in the upward/downward direction, and the grip 202 has a width H2 that is greater than a width H1, as a width in the upward/downward direction. The main body 201 and the grip 202 are configured in such a way that upper faces are located on the same plane, and therefore a position of the main body 201 from the placing surface 800 is higher by a difference between the width H1 and the width H2. Stated another way, when a lower face of the display 203 and a lower face of the grip 202 are placed to abut onto the placing surface 800, a leading-end portion of the main body 201 does not come into contact with the placing surface 800.

This can prevent the leading-end portion of the main body 201 from being contaminated.

Furthermore, in FIG. 8, the tongue depressor 315 of the auxiliary tool 300 is formed to project downward from the lower face of the main body 312 by a distance D3. On the other hand, the lower face of the main body 312 of the tongue depressor is attached to be spaced apart from the placing surface 800 by a distance D4 in a state where the main body 312 is attached to the main body 201 of the image capturing device 200. In this case, the tongue depressor 315 is formed in such a way that the distance D3 is shorter than the distance D4, and this can prevent the tongue depressor 315 from coming into contact with the placing surface 800, and being contaminated.

6. Configuration of Light Source 212

Figure 9:
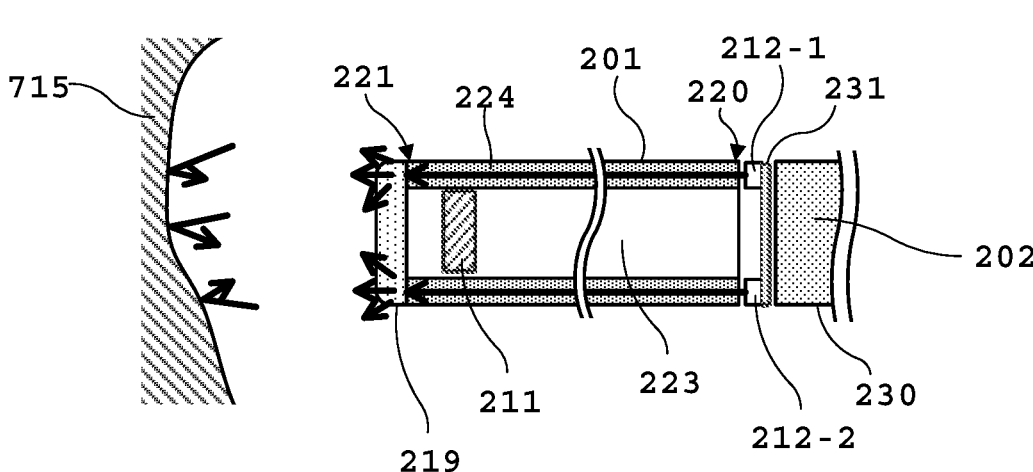
FIG. 9 is a schematic diagram illustrating a sectional configuration of the image capturing device 200 according to the embodiment of the present disclosure.

FIG. 9 is a schematic diagram illustrating a sectional configuration of the image capturing device 200 according to the embodiment of the present disclosure. As illustrated in FIG. 9, as the light source 212, four light sources 212-1 to 212-4 in total are disposed on a substrate 231 that is disposed on a leading end side of the grip 202. Each of the light sources 212 is constituted, as an example, by an LED, and light having a prescribed frequency band is applied from each of the LEDs toward the oral cavity. Specifically, light applied from the light source 212 enters the base end 225 of the main body 201, and is guided toward the diffusion plate 219 by the wall 224 of the main body 201. Light that has reached the diffusion plate 219 is diffused into the oral cavity by the diffusion plate 219. Then, light that has been diffused by the diffusion plate 219 is reflected on a pharynx 715 or the like serving as a subject. This reflected light has reached the camera 211, and this causes a subject image to be generated.

Note that the light sources 212-1 to 212-4 may be configured to be independently controlled. For example, some of the light sources 212-1 to 212-4 are turned on, and this enables a subject image to include a shadow of the subject (influenza follicle or the like) having a stereoscopic shape. This causes the subject image to include information relating to the stereoscopic shape of the subject, and the subject can be more definitely recognized, and a probability of having influenza can be more accurately determined according to a determination algorithm.

Furthermore, in the present embodiment, the light sources 212-1 to 212-4 are disposed on a side of the base end 225 of the main body 201, but may be disposed at the leading end 222 of the main body 201 or in the main body 201 (this may be an inside of the main body 201 or an outer periphery of the main body 201).

In the present embodiment, the diffusion plate 219 is used to prevent light applied from the light source 212 from illuminating only a portion in the oral cavity, and generate uniform light. Accordingly, as an example, a lens-shaped diffusion plate that includes a fine lens array on a surface of the diffusion plate 219, and has an arbitrary angle of diffusion is used. Alternatively, a diffusion plate that can diffuse light by using another method, such as a diffusion plate that achieves a light diffusion function by using fine unevenness that is disposed at random on a surface, may also be used. Moreover, the diffusion plate 219 may be configured integrally with the main body 201. For example, this can be achieved by using a method for forming fine unevenness in the leading-end portion of the main body 201 or another method.

Furthermore, in the present embodiment, the diffusion plate 219, is disposed on a side of the leading end 222 of the main body 201. However, this is not restrictive, the diffusion plate 219 may be disposed in any position between the light source 212 and the inside of the oral cavity serving as its irradiation target, and may be disposed, for example, at the leading end 222 of the main body 201 or in the main body 201 (this may be the inside of the main body 201 or the outer periphery of the main body 201).

7. Configuration of Display 203

Figure 10:
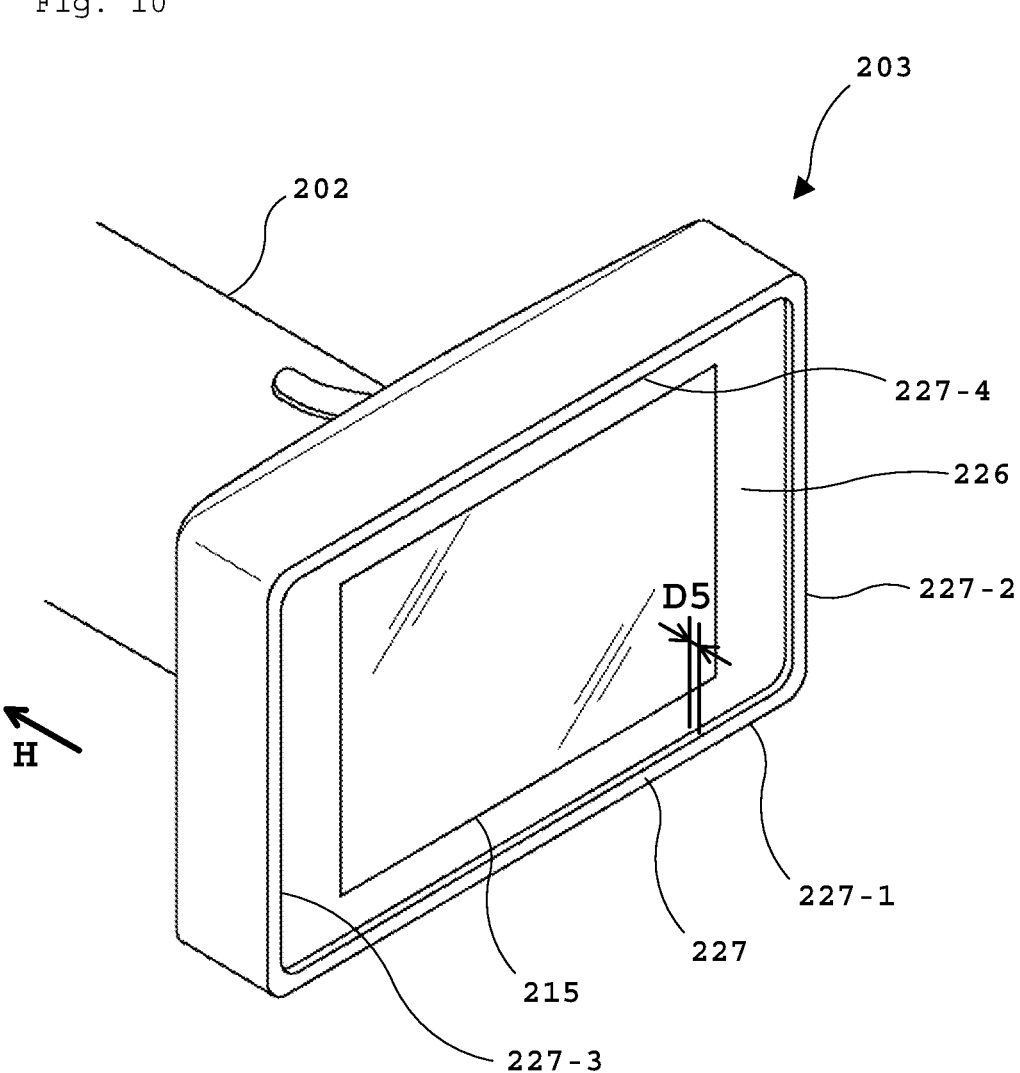
FIG. 10 is a perspective view illustrating a configuration of a display 203 of the image capturing device 200 according to the embodiment of the present disclosure.

FIG. 10 is a perspective view illustrating a configuration of the display 203 of the image capturing device 200 according to the embodiment of the present disclosure. The display 203 is disposed on a base end side of the grip 202 (on a side opposite to the direction H of insertion into the oral cavity). The display 203 has an approximately rectangular parallelepiped shape as a whole, and includes the display panel 215 that is formed in a rectangular shape on a face on a user's side (a side opposite to a side of coupling of the grip 202). On the display panel 215, a subject image captured by the camera 211 is displayed, and as described above, the main body 201, the grip 202, and the display 203 are disposed on the same straight line, and therefore images can be easily captured by using the image capturing device 200 while the subject image displayed on the display 203 is being checked.

Furthermore, a frame 226 is disposed on a periphery of the display panel 215 of the display 203, and a base 227 is formed along a periphery of the frame 226. This base 227 is formed to project from a surface of the display panel 215 by a height D5 toward a user's side, that is, toward a side opposite to the direction H of insertion into the oral cavity. The base 227, as described above, is provided in a position that faces each of at least three sides (in the example of FIG. 10, all of the four sides) of respective sides of the display panel 215 formed in a rectangular shape (bases 227-1 to 227-4).

Note that in FIG. 10, the base 227 is configured as a continuous base along an outer periphery of the display panel 215. However, as described above, it is sufficient if the base 227 is provided in a position that faces at least three sides of respective sides of the display panel 215. Accordingly, the base 227 does not always need to be continuously formed, and may be provided only on portions of the respective sides.

Figure 11:
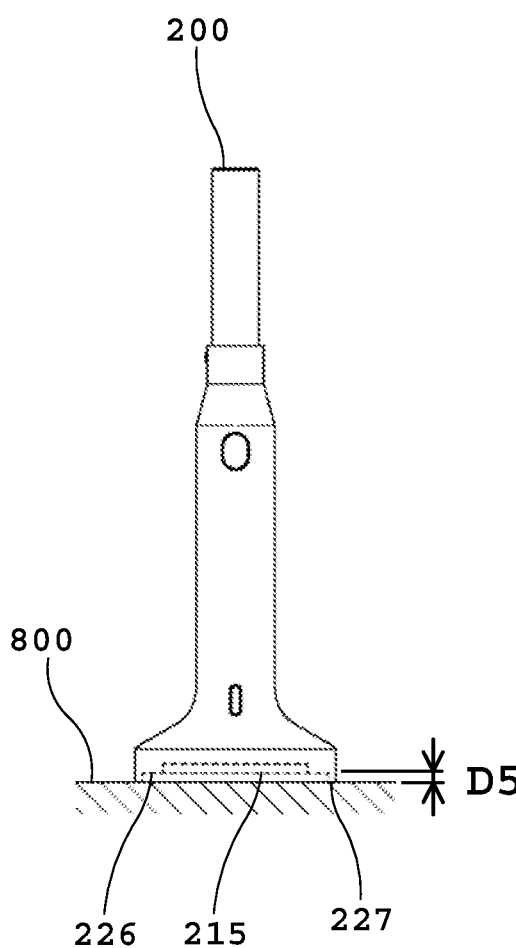
FIG. 11 is a diagram illustrating a placing state of the image capturing device 200 according to the embodiment of the present disclosure.

FIG. 11 is a diagram illustrating a placing state of the image capturing device 200 according to the embodiment of the present disclosure. Specifically, FIG. 11 is a diagram illustrating a case where the image capturing device 200 is placed on the placing surface 800 in such a way that the main body 201 is located on an upper side, and the display 203 is located on a lower side. As described with reference to FIG. 10, the frame 226 is formed along the periphery of the display panel 215, and the base 227 is further formed along the periphery of the frame 226. The base 227 is formed to be higher by the height D5 than the surface of the display panel 215. Therefore, when the base 227 is placed on the placing surface 800, a surface of the base 227 comes into contact with the placing surface 800, and this prevents the display panel 215 from coming into direct contact with the placing surface 800. Stated another way, the base 227 can prevent the display panel 215 from being damaged.

Furthermore, as illustrated in FIG. 11, the entirety of the base 227 is formed to have an approximately uniform height from four sides that form a plane on a user's side of the display 203 formed in a rectangular parallelepiped shape. Accordingly, in placing the image capturing device 200 on the placing surface 800 with the plane facing downward, the image capturing device 200 can be stably placed on the placing surface 800 without particularly using another member such as a placing table.

8. Configuration of Placing Table 400

Figure 12A:
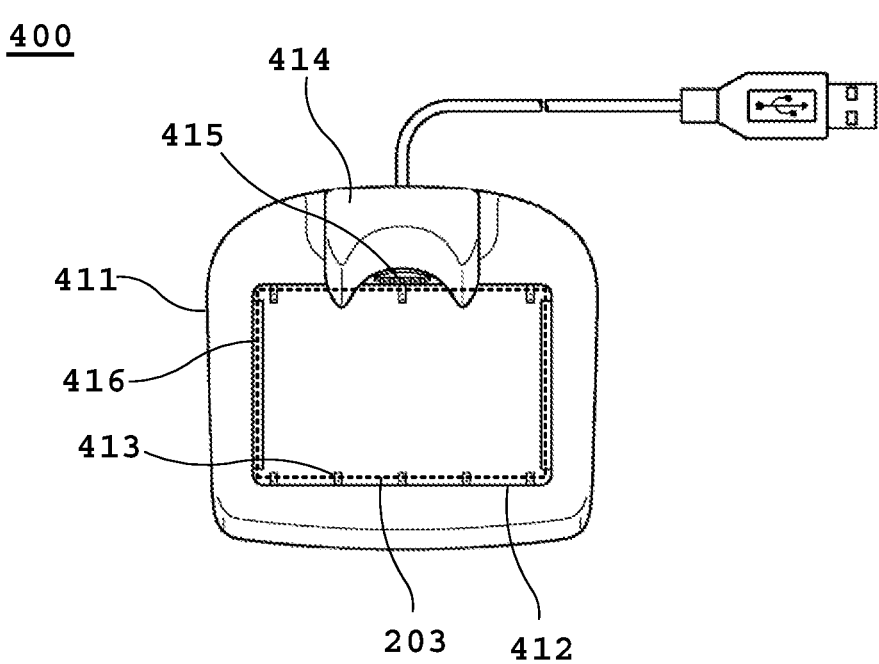
FIG. 12A is a top view illustrating a configuration of a placing table 400 according to the embodiment of the present disclosure.
Figure 12B:
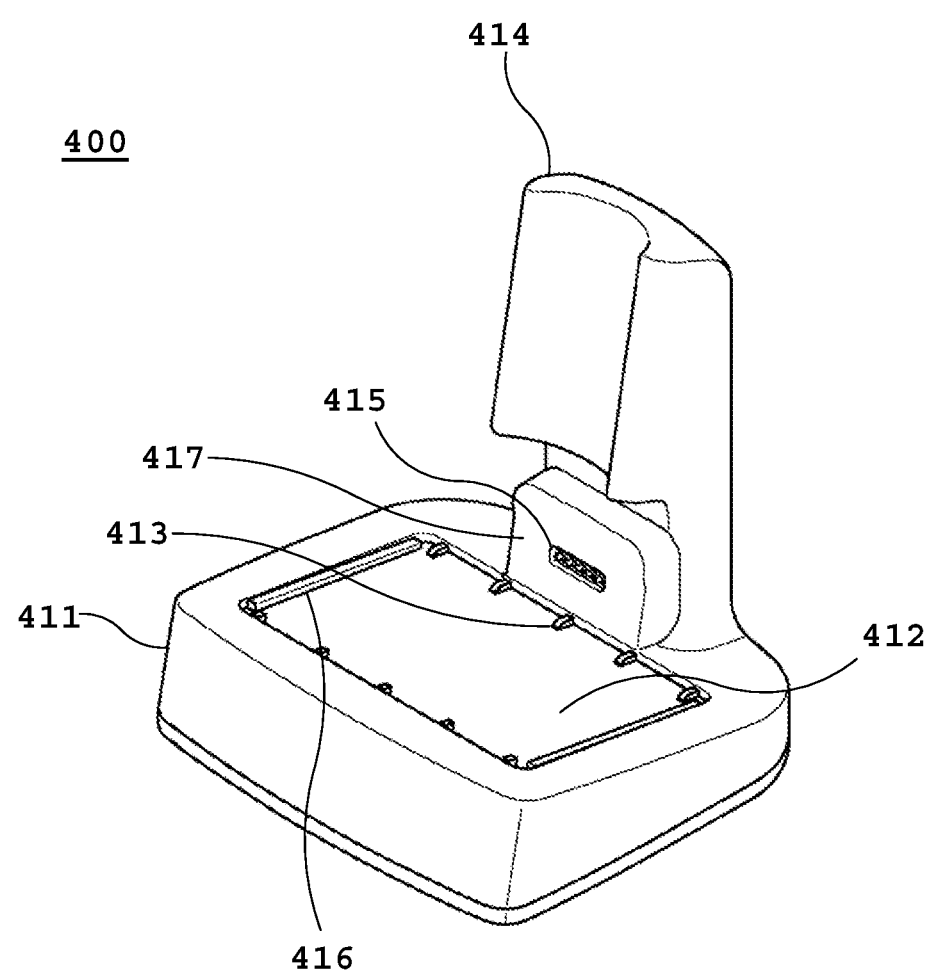
FIG. 12B is a perspective view illustrating the configuration of the placing table 400 according to the embodiment of the present disclosure.

FIG. 12A is a top view illustrating a configuration of the placing table 400 according to the embodiment of the present disclosure. Furthermore, FIG. 12B is a perspective view illustrating the configuration of the placing table 400 according to the embodiment of the present disclosure. The placing table 400 is used to cause the image capturing device 200 to be stably placed, and be connected to a power supply via a wired cable as needed to supply power from the power supply terminal of the placing table 400 through the power supply port of the image capturing device 200 to the image capturing device 200.

As illustrated in FIGS. 12A and 12B, the placing table 400 includes a support table 411 that supports the image capturing device 200 from below and constitutes a main body of the placing table. The support table 411 is formed in an approximately rectangular parallelepiped shape as a while, but this shape is not restrictive, and another shape may be employed. The support table 411 includes a housing hole 412 on the upper face in order to cause the image capturing device 200 to be placed in such a way that the main body 201 of the image capturing device 200 is located on an upper side, and the display 203 is located on a lower side. The housing hole 412 is formed in such a way that a shape of a side wall of the housing hole 412 has a prescribed depth along an outer shape (a broken line in FIG. 12A) of the display 203 of the image capturing device 200. Therefore, if the image capturing device 200 is placed on the placing table 400, the image capturing device 200 is positioned by the side wall of the housing hole 412. Furthermore, the housing hole 412 includes, on a bottom face, one or more projections 413 having a prescribed height (this is lower than a height of the side wall), and one or more linear projections 416 similarly having the prescribed height (this is lower than a height of the side wall). The projection 413 and the linear projection 416 are provided in positions that correspond to the base 227 that is provided on the user's side of the display 203, and support the base 227 from below. Accordingly, between the display panel 215 of the display 203 and the bottom face of the housing hole 412, a space is formed to have the height of the base 227 and the heights of the projection 413 and the linear projection 416. This can prevent the display panel 215 from being damaged by the bottom face of the housing hole 412.

The placing table 400 includes a support stand 414 that supports the vicinity of the grip 202 of the image capturing device 200 from a side, when the image capturing device 200 is placed in the housing hole 412 in such a way that the main body 201 of the image capturing device 200 is located on the upper side and the display 203 is located on the lower side. The support stand 414 is disposed above the support table 411, and is formed to have a prescribed length in a height direction. Furthermore, a face that faces the grip 202 is formed along an outer shape of the grip 202. Note that the support stand 414 itself does not need to always come into contact with the vicinity of the grip 202 of the image capturing device 200 and continue to support the grip 202, and it is sufficient if the support stand 414 comes into contact with the grip 202, for example, when the image capturing device 200 is tilted.

The placing table 400 includes a power supplier 417 in a position facing a lower face of the display 203 of the image capturing device 200 (that is, a face on which the power supply port 228 is disposed) in a state where the image capturing device 200 is placed in the housing hole 412. The power supplier 417 includes a power supply terminal 415 in a position that faces the power supply port 228 of the image capturing device 200 on a face on a side facing the lower face of the display 203. Accordingly, when the image capturing device 200 is placed in the housing hole 412, the power supply port 228 is coupled to the power supply terminal 415 of the placing table 400, and power is supplied from the power supply terminal 415 to the power supply port 228.

Here, as described with reference to FIG. 6D, the input/output terminal 229 is disposed on the lower face of the display 203 of the image capturing device 200, that is, the same face as the face on which the power supply port 228 is disposed. If the image capturing device 200 is placed in the housing hole 412, the power supply port 228 is coupled to the power supply terminal 415 that is disposed in a position facing the power supply port 228, but the input/output terminal 229 is covered with a face on a side facing the lower face of the display 203 in the power supplier 417. Therefore, when power is supplied via the power supply port 228, wired connection of the input/output terminal 229 becomes unavailable, and this can avoid competition with power via the input/output terminal 229.

As described above, according to the present embodiment, the image capturing device 200 and the image capturing system 1 better suited to capturing images in the oral cavity can be provided. In particular, respective members including the main body 201, the grip 202, the display 203, and the camera 211 and the main body 201 are disposed on the same straight line in a direction of insertion into the oral cavity. This enables satisfactory operability to be provided to an operator.

Other Embodiments

In the embodiment described above, a case where the processing device 100 and the image capturing device 200 are communicably connected wirelessly or through a wired cable has been described. However, this is not restrictive, and a subject image captured by the image capturing device 200 can be transmitted to a server device that has been remotely installed (for example, a cloud server device) via wireless communication, and the server device can be caused to function as a processing device. Specifically, disease likelihood can be determined by using the server device, or can be determined together with a physician's observations by transmitting the subject image to a terminal device for physicians that has been remotely equipped, and causing the terminal device to function as the processing device.

Furthermore, in the embodiment described above, a case where the processing device 100 and the image capturing device 200 are communicably connected wirelessly or through a wired cable, and the processing device 100 processes a subject image has been described. However, this is not restrictive, and the image capturing device 200 itself can have various functions of processing the subject image. For example, the image capturing device 200 itself may be equipped with a determination function of the processing device 100 to determine disease likelihood. In this case, a processed image may be output to the processing device 100 or another device that is connected in a wired or wireless manner.

Moreover, in the present embodiment, a case where the image capturing device 200 and the auxiliary tool 300 are separately configured has been described. However, this is not restrictive, and both may be integrally configured. For example, in the image capturing device 200, a ton depressor that regulates a movement of the tongue in the oral cavity may be disposed on a face on a tongue side of the main body 201 in such a way that the tong depressor is located on the tongue side in the oral cavity. This enables image capturing without using the auxiliary tool 300.

REFERENCE SIGNS LIST

1 Image capturing system
100 Processing device
111 Processor
112 Memory
113 Input interface
114 Display
115 Communication interface
200 Image capturing device
201 Main body
202 Grip
203 Display
211 Camera
212 Light source
212-1 Light source
213 Processor
214 Memory
215 Display panel
216 Communication interface
217 Engagement projection
217-1 Engagement projection
218 Positioning projection
219 Diffusion plate
220 Image capturing button
221 Power button
222 Leading end
223 Housing space
224 Wall
225 Base end
226 Frame
227 Base
227-1 Base
228 Power supply port
229 Input/output terminal
230 Coupling portion
231 Substrate
232 Housing space
300 Auxiliary tool
311 Grasping plate
312 Main body
313 Leading-end side opening
314 Leading end
315 Tongue depressor
316 Base end
317 Piece
317-1 Piece
318 Engagement projection
318-1 Engagement projection
319 Groove
319-1*a* Groove
320 Base-end side opening
321 Insertion hole
400 Placing table
411 Support table
412 Housing hole
413 Projection
414 Support stand
415 Power supply terminal
416 Linear projection
417 Power supplier
600 User
700 Target person
711 Incisor
712 Oral cavity
713 Soft palate
714 Tongue
715 Pharynx
800 Placing surface

What is claimed is:

1. An image capturing device comprising:
a main body including a base end and a leading end, being formed in a hollow columnar shape having a wall defining a housing space within an inner surface of the wall, the main body having a prescribed length between the base end and the leading end, and wherein in use, a longitudinal direction of the main body is configured to be located along a direction of insertion into an oral cavity to enable at least the leading end to be inserted into the oral cavity;
one or more light sources configured to apply light having a prescribed frequency band toward the oral cavity, the one or more light sources being disposed at the base end of the main body or inside the main body, the light being guided within the wall from a position adjacent to the base end toward the leading end of the main body;
a grip configured to be grasped by a user, the grip being formed in an approximately columnar shape having a prescribed length, the grip elongating from the base end of the main body along the longitudinal direction of the main body, the grip and the main body being disposed on an identical straight line;
a camera disposed in the housing space of the main body and facing in a direction along the longitudinal direction of the main body, the camera being configured to capture a subject image based on reflected light applied from the one or more light sources and reflected on the oral cavity, the camera and the main body being disposed on the identical straight line; and
a display configured to display the subject image captured by the camera, the display being disposed on a side of the grip opposite to the base end of the main body, the display and the main body being disposed on the identical straight line.

2. The image capturing device according to claim 1, wherein the subject image is an image indicating a pharynx.

3. The image capturing device according to claim 1, wherein the prescribed frequency band is an ultraviolet light band.

4. The image capturing device according to claim 1, wherein
the display includes:
a display panel configured to display the subject image; and
a base including at least a portion on a periphery of the display panel projecting from a surface of the display panel in a direction away from the main body.

5. The image capturing device according to claim 4, wherein
the display panel is formed in a rectangular shape, and
the base projects from each side of the display panel formed in the rectangular shape.

6. The image capturing device according to claim 4, wherein the base is configured to prevent the display panel from coming into direct contact with a placing surface, when the image capturing device is placed on the placing surface with the display located against the placing surface and the main body located away from the placing surface.

7. The image capturing device according to claim 4, wherein the base is configured to support the image capturing device when placed on a placing surface with the display located against the placing surface and the main body located away from the placing surface without using a placing table for placing the image capturing device thereon.

8. The image capturing device according to claim 1, wherein the grip includes a grip housing space configured to house a battery.

9. The image capturing device according to claim 8, wherein, when the image capturing device is placed in a horizontal direction in a state where the subject image is displayed on the display in an ordinary orientation, the grip housing space is located below a center axis of the main body along the longitudinal direction.

10. The image capturing device according to claim 1, wherein the grip includes an image capturing button located on a side of an upper face of the grip when an orientation where the subject image is displayed on the display is an ordinary orientation.

11. The image capturing device according to claim 1, wherein at least a portion of the image capturing device is configured to be inserted into and covered by an auxiliary tool having a tubular shape, and the auxiliary tool elongates along the longitudinal direction of the main body.

12. The image capturing device according to claim 1, wherein the image capturing device includes a power supply port configured to supply power to the image capturing device from outside.

13. The image capturing device according to claim 12, wherein the power supply port is configured to be coupled to and receive the power from a power supply terminal of a placing table when the image capturing device is placed on the placing table with the display located within a housing hole of the placing table and the main body located away from the placing table.

14. The image capturing device according to claim 12, wherein the image capturing device includes an input/output terminal configured to transmit or receive information to/from outside in a wired manner, and the power supply port and the input/output terminal are disposed on an identical plane of an outer periphery of the display.

15. An image capturing system comprising:

the image capturing device according to claim 1; and a processing device configured to process the subject image captured by the image capturing device, the processing device being communicably connected to the image capturing device in a wired or wireless manner.

16. The image capturing device according to claim 1, wherein the one or more light sources are disposed at the base end of the main body, and the light is guided within the wall from the base end to the leading end of the main body.

17. The image capturing device according to claim 1, wherein the display has a display panel, and the display panel of the display faces in a direction along the longitudinal direction of the main body.

* * * * *